United States Patent [19]

Champetier et al.

[11] Patent Number: 4,917,499

[45] Date of Patent: Apr. 17, 1990

[54] APPARATUS FOR ANALYZING CONTAMINATION

[75] Inventors: Robert J. Champetier, Torrance; Richard L. Graff, Ventura, both of Calif.

[73] Assignee: Hughes Aircraft Company, Los Angeles, Calif.

[21] Appl. No.: 914,900

[22] Filed: Oct. 3, 1986

[51] Int. Cl.[4] .......................................... G01N 25/00
[52] U.S. Cl. ............................................ 374/14; 73/23; 73/25
[58] Field of Search ............ 374/14, 16, 22, 23, 374/27; 73/25, 26, 23, 23.1; 310/341

[56] References Cited

U.S. PATENT DOCUMENTS

| | | | |
|---|---|---|---|
| 3,459,033 | 8/1969 | Stuart | 73/25 |
| 3,478,573 | 11/1969 | King | 73/26 |
| 3,519,547 | 7/1970 | Paulik et al. | 374/14 |
| 3,689,907 | 9/1972 | Guajardo | 374/23 |
| 3,715,911 | 2/1973 | Chuan | 73/28 |
| 3,828,607 | 8/1974 | Janzen et al. | 73/23 |
| 3,904,364 | 9/1975 | Dodson | 374/14 |
| 4,214,473 | 7/1980 | Edwards et al. | 73/23 |
| 4,227,398 | 10/1980 | Keirns et al. | 73/61 R |
| 4,558,589 | 12/1985 | Hemmes | 374/23 |
| 4,561,286 | 12/1985 | Sekler et al. | 73/23 |
| 4,596,697 | 6/1986 | Ballato | 422/98 |

FOREIGN PATENT DOCUMENTS

| | | |
|---|---|---|
| 0119772 | 9/1984 | European Pat. Off. . |
| 1066124 | 4/1967 | United Kingdom . |
| 2080532 | 2/1982 | United Kingdom ............ 73/23 |

OTHER PUBLICATIONS

Wallace Donald A., "Miniature Quartz Crystal Microbalance for Contamination Measurement," *Journal of Spacecraft and Rockets*, vol. 17, No. 2, Mar.-Apr. (1980) pp. 153-156.

Bradley et al, Automated Thermoanalytical Techniques: An Automated Thermobalance, Analytical Chemistry, vol. 43, NO. 2, Feb. 1971 pp. 223-227.

Primary Examiner—William A. Cuchlinski, Jr.
Assistant Examiner—Patrick R. Scanlon
Attorney, Agent, or Firm—William J. Streeter; Wanda K. Denson-Low

[57] ABSTRACT

An apparatus (10) for identifying molecular contamination in an environment includes a pair of crystals (12, 14) supported within supports (16, 18, 20) which are cantilevered to a base (44) by standoffs (36). Base is housed within an enclosure (56) which opens through an opening (54) to an environment to be tested. Contaminants from the environment are deposited on sensing crystal (12) which, after a build up of the contaminants thereon, is heated by a heater. Through a thermo-gravimetric analysis, the points at which contaminants on crystal (12) sublime provide a means for identifying the contaminants.

13 Claims, 2 Drawing Sheets

APPARATUS FOR ANALYZING CONTAMINATION

BACKGROUND OF THE INVENTION

This invention was made with Government support under a contract awarded by the Department of Defense. The Government has certain rights in this invention.

The present invention relates to apparatus for analyzing contaminants, in particular, in cryogenic environments in the temperature range of less than 10° K. to over 350° K.

It is important to keep equipment as clean as possible from contamination, such as optical and electrooptical apparatus, which may be in a relatively inaccessable place, such as in space. Such contamination may occur by residual outgassing of spacecraft materials, which can build up to such an extent as to interfere with proper use of the equipment. Removal of such contaminants depends upon their identification.

It is also desirable during development in the laboratory to have a diagnostic tool which can be used as an aid in the design of such components as cryogenic sensors so that remedies can be implemented therein prior to their being incorporated into the system and delivered to a customer. For more general applications, it is often useful in laboratory or industrial use or, wherever a process may be affected by contamination, to identify the contaminant in real time in the vacuum and cryogenic system.

Contamination sensing has utilized miniature quartz crystal microbalances in vacuum cryogenic hardware to detect the mass of the contaminant layer, but not its composition.

Identification of contamination within the working environment of the equipment and in remote environments, such as in space, or under special circumstances such as for in-process laboratory detection, has been heretofore precluded.

It is therefore desirable to obtain such identification of molecular contamination under actual test or operation of the equipment.

SUMMARY OF THE INVENTION

The present invention combines such a quartz crystal microbalance and thermo-gravimetric analysis in a self-contained package as an autonomous device, while simultaneously decreasing the package size, to enable its mounting into association with any electro-optical device, with reduced power requirements.

Specifically, sensing and reference crystals, a heater and a temperature sensor therefor are held away from a supporting base by low thermal conductance supports. Electronics, such as an oscillator and a mixer, are supported on the base. Leads from the electronics and the heater extend outside the package to power and heater supplies and a read-out. The sensing crystal is exposed the environment and any contamination therein, without power being applied to the heater, so that contaminants can deposit on the crystal to form a cryofilm thereon. After a build up for any desired period of time, a thermo-gravimetric analysis is begun by applying power to the heater and thereby gradually to warm up the sensing crystal and the film of condensed contaminants thereon. At critical sublimation temperatures of the various contaminants, they evaporate, and their loss and therefore a total decrease of mass of crystal and contaminant is perceived as a change in the frequency of the sensing crystal. Differentiating the deposit mass with respect to time provides a spectrum which enables the several contaminants to be identified either specifically (e.g. carbon dioxide) or generally (organic material).

Several advantages are obtained thereby. Because both crystals, the heater and electronics therefor are placed together, they can be contained in a small package. Detection and identification of contaminants occur without removal of the package from the environment and, after testing has been completed, the power to the heater may be turned off in order to cool the quartz crystal microbalance and thus to permit a build-up of further contaminants. The state of the apparatus under investigation can be monitored so that the invention can be utilized as a predictive tool. For example, if the cryofilm is known to absorb radiation in the wavelength band operation of the equipment, e.g., a telescope, degradation of its performance can be predicted and, if necessary, compensated for.

Other aims and advantages as well as a more complete understanding of the present invention will appear from the following explanation of an exemplary embodiment and the accompanying drawings thereof.

DETAILED DESCRIPTION OF THE INVENTION

Figure 1:
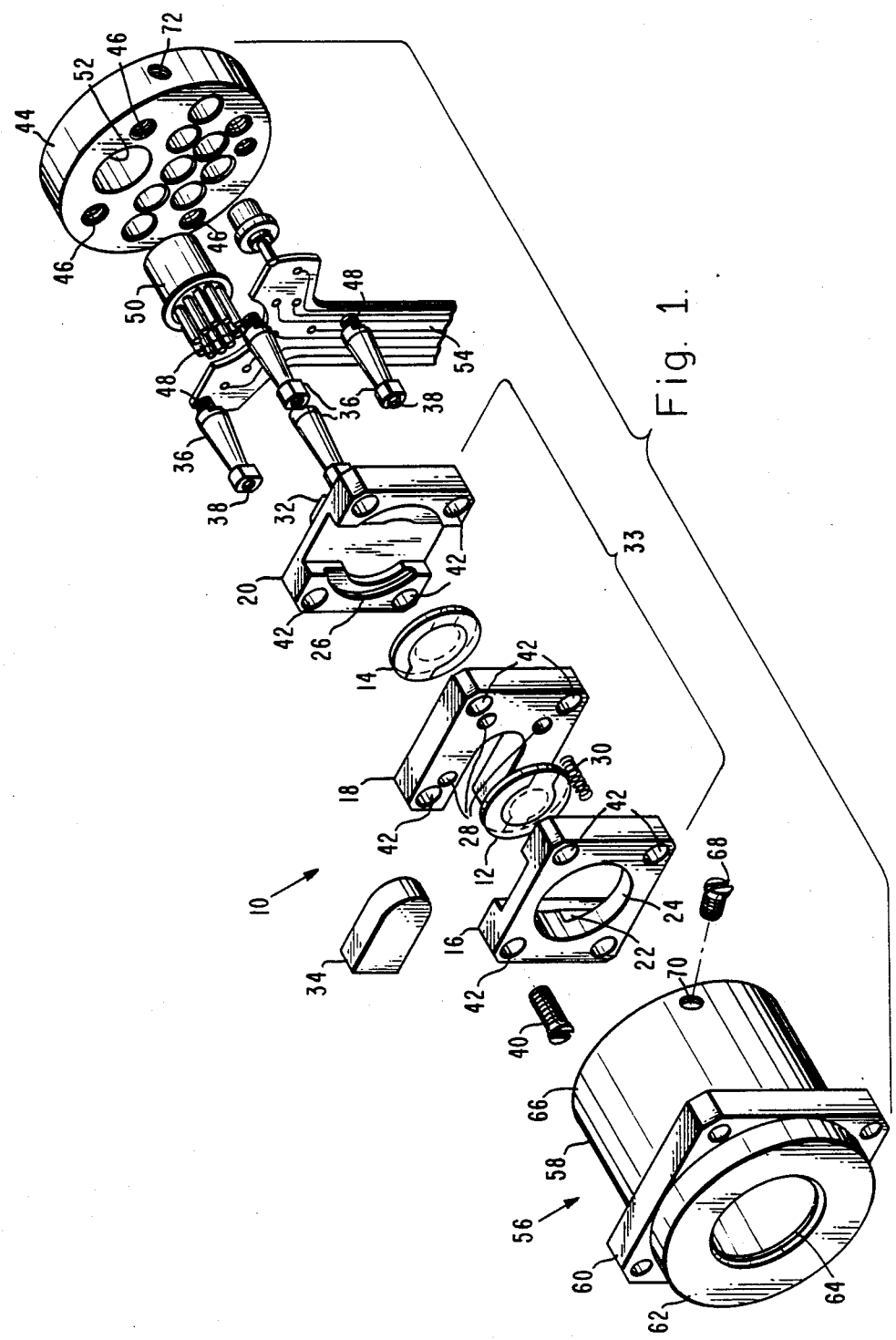
FIG. 1 is an exploded, three dimensional view of the present invention.
Figure 2:
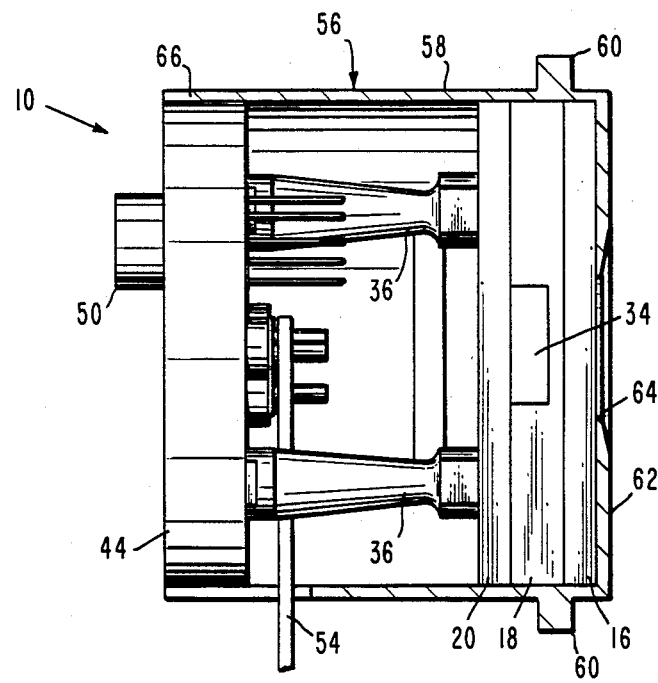
FIG. 2 is a side elevational view in partial cross-section depicting the present invention.

Referring to FIGS. 1 and 2, an apparatus 10 includes a pair of crystals, a sensing crystal 12 and a reference crystal 14, which are supported within a supporting structure comprising a first support 16, a second intermediary support 18 and a third, heaterbearing support 20. A recess 22 in first support 16 receives sensing crystal 12, and an opening 24 in the first support exposes a front surface of the sensing crystal to the environment under consideration and onto which contaminants are to be deposited. Third support 20 also has a recess 26 into which reference crystal 14 resides.

Second support 18 is provided with a plurality of through openings 28 through which a plurality of springs 30 extends. The ends of the springs extend on either side of second support 18 and bear against respective crystals 12 and 14 to urge them into their respective recesses 22 and 26. The springs are disposed to provide an even distribution of forces against the crystals and, thus, to relieve them of any possible distorting stresses which may otherwise be exerted thereon.

Third support 20 is provided with an opening 32 for receipt of a heater, such as a wire wound element or equivalent, so that the sensing package 33 formed by supports 16, 18 and 20 may be isothermally heated. A temperature sensor 34 is positioned in second support 18 for sensing the temperature on sensing package 33. Four standoffs 36 have internally threaded recesses 38 at one of their ends and threaded shafts 48 at their other ends. Threaded recesses 38 provide the fastening means along with bolts 40 for securing supports 16, 18 and 20 and crystals 12 and 14 into a unitary package. Specifically, bolts 40 extend through holes 42 in all supports 16, 18 and 20 and thread into threaded recesses 38 of respective standoffs 36.

A base 44 is provided with threaded holes 46 into which ends 48 of standoffs 36 are threaded. Therefore, base 44 supports sensing package 33 through standoffs 38 in a cantilevered fashion. A quartz crystal microbalance (QCM) oscillator-mixer 50 utilizing CMOS technology is force-fitted within a hole 52 within base 44 and is appropriately electrically coupled to crystals 12 and 14. A flat cable 54 extends from the assembly to external power and heater supplies and a readout. The assembly as secured to base 44 is housed within an enclosure 56 including a case 58 and an external flange 60, all which is adapted to be affixed to a wall of an environment to be tested. Case 58 as a forward wall 62, which is open at 64 to the environment in order to expose a surface of sensing crystal 12 thereto. Base 44 fits within the other end 66 and is retained by screws 68 which extend through holes to in case 58 and into engagement with threaded holes 72 in base 44.

The operation of apparatus 10 is shown with respect to the curves depicted in FIGS. 3a–3c, in which curve 80 represents the temperature of crystal 12, curve 82 represents the initial build up and later sublimation of contaminants on and from crystal 12, and curve 84 represents a readoff identifying the type or character of the contaminants as they sublime. Initially, in the use of apparatus 10, no power is supplied to the heater, so that the assembly can approach the temperature of the surface to which flange 60 is attached. This point may be represented by portion 80a of curve 80 at, for example, 10° K. Contaminants build up as a cryofilm on the exposed surface of crystal 12, as illustrated by portion 82a of curve 82. Such a build up is permitted for any desired time, which may last for a few hours up to several months (depicted by the broken portion of the abscissa), at which time a decision is made to identify the constituency of the contaminants.

Thus, the build up is permitted to reach a level indicated by curve portion 82b. At this point, the temperature of the environment comprising sensing package 33 is increased, by applying power to the heater as illustrated by the gradual rise of curve 80. A linear temperature rise is shown as portion 80b; however, the temperature rise need not be gradual but could be in steps. At a critical contaminant sublimation temperature, a contaminant will sublime, and its evaporation is shown as a loss in mass indicated by the reduced level of curve 82 from level 82b to level 82c. This loss of build up on crystal 12, as referenced to reference crystal 14, is denoted by a change in frequency of crystal 12 and indicates a temperature at which the contaminant sublimes. Because specific elements or compositions of matter have different temperatures as changing from one of their solid-liquid-vapor states to another one of these states, the sublimation temperature provides an indication of what that contaminant is.

Figure 3:
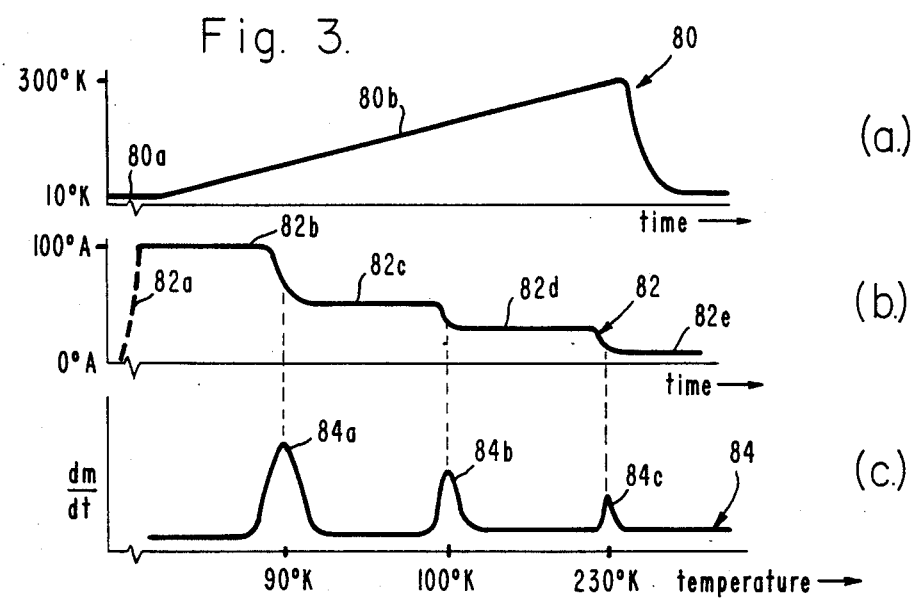
FIGS. 3a–3c are graphic representations respectively of the time versus temperature increase to be applied to the sensing crystal, the build up and later sublimation of contaminants on and from the sensing crystal with respect to the time and temperature curve of FIG. 3a, and the detection of the contaminants as they sublime from the sensing crystal.

For example as shown in FIG. 3c, at an illustrated temperature of 90° K., the sublimed contaminant is carbon dioxide and is devoted by spike 84a of curve 84. As the heater is further warmed, another contaminant will sublime so as to provide a reduced build up level at curve level 82d. This loss may, for example, occur at 160° K., which is sublimation temperature of water identified by spike 84b of curve 84. Additional warming of the heater may indicate a further loss of contaminant build up to a level of 82e, providing a spike 84c at 230° K., which is indicative of an organic contaminant. Thus, at critical temperatures, contaminants and their losses are perceived as changes in mass and frequency of crystal 12. Differentiating the deposit mass with respect to time provides a mass to time ratio (dm/dt), which is the thermo-gravimetric analysis spectrum. At the end of the analysis, the quartz crystal microbalance may be re-cooled for new testing.

Although the invention has been described with reference to a particular embodiment thereof, it should be realized that various changes and modifications may be made therein without departing from the spirit and scope of the invention.

What is claimed is:

1. Apparatus for identifying molecular contamination in an environment comprising a unitary package including:

a sensing crystal for collecting the contamination;

means for causing the contamination to change from one of its solid-liquid-vapor states to another of its solid-liquid-vapor states;

means including a reference crystal spaced from said sensing crystal for providing a reference comparison therfor, for conducting a thermo-gravimetric analysis on said sensing crystal and the contamination thereon and for vibrating said sensing crystal and detecting its frequency of vibration and any changes therein, thereby for detecting the change of state to identify the contamination; and an enclosure having means for supporting said sensing crystal and for exposing said sensing crystal to the environment, and comprising a base;

means for supporting said reference crystal, and means for spacing said sensing and reference crystals and said supporting means therefor in substantial thermal isolation from said base, and in which said supporting means comprise a first support supporting said sensing crystal, a second support secured to said first support, a third support secured to said second support and supporting said reference crystal, and resilient means extending through said second support in contact with both said crystals and biasing said crystals respectively into contact with their respective supports.

2. Apparatus according to claim 1 in which said resilient means comprises springs extending through said second support.

3. Apparatus according to claim 1 in which said spacing means includes standoffs secured at opposite ends to said base and to said third support for spacing said third support and said crystals from said base for providing the substantial thermal isolation of said crystals from any undesired heating thereof.

4. Apparatus according to claim 3 in which said contamination change causing means includes a heater coupled to the environment of said sensing crystal for causing the contamination of sublime from said sensing crystal.

5. Apparatus according to claim 4 further including a temperature sensor housed in said second support.

6. Apparatus according to claim 5 in which said enclosure further includes a tubular case having a forward wall with an opening therein, a rear opening and a flange for attaching said enclosure to an opening to the environment;

said base with attached crystals and crystal supporting means is housed within said case to position said sensing crystal adjacent the opening in said case forward wall; and means for securing said base to said case to provide a cantilevered support of said crystals in said enclosure.

7. Apparatus according to claim 6 in which said vibrating means includes an oscillator and mixer secured to said base for exciting said crystals and sensing the relative vibrational frequencies thereof and the mass of said crystal before, during and after said heater heats the environment of said sensing crystal gradually for permitting different types of contamination to sublime at their characteristic temperatures.

8. Apparatus for identifying molecular contamination in an environment comprising a unitary package including:

means for collecting the contamination;

means for causing the contamination to change from one of its solid-liquid-vapor states to another of its solid-liquid-vapor states;

means for detecting the change of state to identify the contamination; and an enclosure having a base, means for supporting said collecting means, said contamination change causing means and said detecting means, and for exposing said collecting means to the environment, and means for spacing said supporting means in substantial thermal isolation from said base, said supporting means comprising a first support supporting said collection means, a second support secured to said first support, a third support secured to said second support and supporting said detecting means, and resilient means extending through said second support in contact with both said collection means and said detection means and biasing said collection means and said detection means respectively into contact with their respective supports.

9. Apparatus according to claim 8 in which said collecting means comprises a sensing crystal and said detecting means includes means for vibrating said sensing crystal and detecting its frequency of vibration and any changes therein.

10. Apparatus according to claim 9 in which said detecting means further includes a reference crystal spaced from said sensing crystal for providing a reference comparison therefor.

11. Apparatus according to claim 10 in which said resilient means is arranged to maintain said crystals in a mutually unstressed condition.

12. Apparatus according to claim 10 in which said resilient means spaces said crystals from one another.

13. Apparatus according to claim 8 in which said causing means comprises a heater for heating the deposited contaminants.

* * * * *